(12) United States Patent
Sekiya et al.

(10) Patent No.: US 10,510,524 B2
(45) Date of Patent: Dec. 17, 2019

(54) ION TRAP MASS SPECTROMETRY DEVICE AND MASS SPECTROMETRY METHOD USING SAID DEVICE

(71) Applicant: SHIMADZU CORPORATION, Kyoto-shi, Kyoto (JP)

(72) Inventors: Sadanori Sekiya, Kyoto (JP); Hidenori Takahashi, Kyoto (JP)

(73) Assignee: SHIMADZU CORPORATION, Kyoto-shi, Kyoto (JP)

(*) Notice: Subject to any disclaimer, the term of this patent is extended or adjusted under 35 U.S.C. 154(b) by 0 days.

(21) Appl. No.: 16/070,659

(22) PCT Filed: Jan. 18, 2016

(86) PCT No.: PCT/JP2016/051269
§ 371 (c)(1),
(2) Date: Dec. 10, 2018

(87) PCT Pub. No.: WO2017/126006
PCT Pub. Date: Jul. 27, 2017

(65) Prior Publication Data
US 2019/0108993 A1    Apr. 11, 2019

(51) Int. Cl.
*H01J 49/42*    (2006.01)
*H01J 49/00*    (2006.01)
*G01N 27/62*    (2006.01)

(52) U.S. Cl.
CPC ............ *H01J 49/427* (2013.01); *G01N 27/62* (2013.01); *H01J 49/0031* (2013.01); *H01J 49/42* (2013.01)

(58) Field of Classification Search
CPC ...... H01J 49/427; H01J 49/0031; H01J 49/42; G01N 27/62

(Continued)

(56) References Cited

U.S. PATENT DOCUMENTS 8,975,575 B2 * 3/2015 Sekiya ............... H01J 49/0481
250/281
2008/0142705 A1 * 6/2008 Schwartz ............ H01J 49/0045
250/292

(Continued)

FOREIGN PATENT DOCUMENTS

JP    2012-049056 A    3/2012
WO   2015/133259 A1   9/2015

OTHER PUBLICATIONS

Raymond E. March et al., "An Introduction to Quadrupole Ion Trap Mass Spectrometry", Journal of Mass Spectrometry, 1997, pp. 351-369, vol. 32.
Li Ding et al., "A digital ion trap mass spectrometer coupled with atmospheric pressure ion sources", Journal of Mass Spectrometry, 2004, pp. 471-484, vol. 39.

(Continued)

*Primary Examiner* — Nicole M Ippolito
(74) *Attorney, Agent, or Firm* — Sughrue Mion, PLLC

(57) ABSTRACT

After various ions of sample origin have been captured within an ion trap, unnecessary ions other than a target ion having a specific m/z are ejected from the ion trap (S1, S2). Subsequently, an operation for dissociating the target ion within the ion trap by hydrogen radical dissociation (HAD), and an operation for sequentially ejecting the thereby generated product ions by resonance excitation from the low m/z side to a point located immediately before the m/z of the target ion, are repeated multiple times (S3-S7). The ions ejected by resonance excitation are detected with a detector to acquire MS/MS spectrum data, and the data obtained by performing the ejection by resonance excitation multiple times are accumulated to create the final MS/MS spectrum (S5, S8).

7 Claims, 5 Drawing Sheets

(58) Field of Classification Search
USPC .................................... 250/281, 282, 283
See application file for complete search history.

(56) References Cited

U.S. PATENT DOCUMENTS

| | | | |
|---|---|---|---|
| 2008/0210860 A1* | 9/2008 | Kovtoun .............. | H01J 49/004 250/283 |
| 2011/0084205 A1* | 4/2011 | Makarov ............. | H01J 49/0045 250/282 |
| 2016/0372311 A1 | 12/2016 | Takahashi et al. | |
| 2018/0277345 A1* | 9/2018 | Li ....................... | H01J 49/0081 |

OTHER PUBLICATIONS

Lekha Sleno et al., "Ion activation methods for tandem mass spectrometry", Journal of Mass Spectrometry, 2004, pp. 1091-1112, vol. 39.

Reiko Kiyonami et al., "Increased Selectivity, Analytical Precision, and Throughput in Targeted Proteomics", Molecular & Cellular Proteomics 10.2, 2011, 10.1074/mcp.M110.002931-1~10.1074/mcp.M110.002931-11.

Melinda A. Mcfarland et al., "Evaluation and Optimization of Electron Capture Dissociation Efficiency in Fourier Transform Ion Cyclotron Resonance Mass Spectrometry", J Am Soc Mass Spectrom 2005, pp. 1060-1066, vol. 16.

International Search Report of PCT/JP2016/051269 dated Mar. 15, 2016 [PCT/ISA/210].

Written Opinion of PCT/JP2016/051269 dated Mar. 15, 2016 [PCT/ISA/237].

* cited by examiner

MS/MS SPECTRUM BY CID

MS/MS SPECTRUM BY HAD

ION TRAP MASS SPECTROMETRY DEVICE AND MASS SPECTROMETRY METHOD USING SAID DEVICE

TECHNICAL FIELD

The present invention relates to an ion trap mass spectrometer including an ion trap capable of capturing ions by the effect of a radio-frequency electric field, as well as a mass spectrometric method using such a mass spectrometer.

BACKGROUND ART

An ion trap mass spectrometer which uses an ion trap capable of capturing ions by the effect of a radio-frequency electric field has been known as one type of mass spectrometer. A typically used ion trap is a three-dimensional quadrupole ion trap, which includes a pair of endcap electrodes facing each other across a doughnut-shaped ring electrode. Another commonly known type of ion trap is a linear ion trap, which includes four rod electrodes arranged parallel to each other, with two endcap electrodes respectively arranged on the outside of the two ends of those rod electrodes. The following description deals with the case of an ion trap mass spectrometer using a three-dimensional quadrupole ion trap unless otherwise noted.

Normally, in an ion trap mass spectrometer, a radio-frequency voltage is applied to the ring electrode while the pair of endcap electrodes are maintained at a potential of 0 V, to create a radio-frequency quadrupole electric field within the inner space of the ion trap and capture ions by the effect of this electric field. It has been commonly known that the behavior of the ions captured within the inner space of the ion trap can be expressed by the Mathieu equation. If the amplitude value of the radio-frequency voltage applied to the ring electrode is gradually increased under the condition that ions are captured within the inner space of the ion trap, the trajectories of the ions become unstable in ascending order of mass-to-charge ratio, and are eventually ejected to the outside through an opening bored in one of the endcap electrodes. By employing this principle, it is possible to separate ions from each other by their mass-to-charge ratios or selectively maintain an ion having a specific mass-to-charge ratio within the inner space of the ion trap (see Non-Patent Literature 1 or other documents).

In many of the conventionally used ion trap mass spectrometers, the radio-frequency voltage applied to the ring electrode is a sinusoidal voltage. Meanwhile, an ion trap mass spectrometer in which a rectangular radio-frequency voltage is applied to the ring electrode is also known, as disclosed in Non-Patent Literature 2 or other documents. Such an ion trap has conventionally been called the "digital ion trap". A mass spectrometer using a digital ion trap can separate ions from each other by their mass-to-charge ratios or selectively maintain an ion having a specific mass-to-charge ratio, by controlling the frequency of the rectangular voltage applied to the ring electrode while maintaining the voltage value (pulse-height value) of the rectangular voltage.

In the previously described types of ion trap mass spectrometers, an MS/MS analysis or MS$^n$ analysis can be performed as follows: Various ions of sample origin are temporarily captured within the ion trap. Among those ions, a target ion with a specific mass-to-charge ratio is selectively maintained within the inner space of the ion trap. This ion is used as a precursor ion and dissociated into product ions within the inner space of the ion trap. The product ions are individually separated by mass and detected. The most commonly used method for dissociating an ion is the collision induced dissociation (CID), in which the dissociation of an ion is promoted by making the ion collide with gas (normally, inert gas). There are also other techniques: a hydrogen radical attachment dissociation (HAD), in which the dissociation of an ion is promoted by irradiation with hydrogen radicals, which are uncharged particles; an electron transfer dissociation (ETD) or electron capture dissociation (ECD), in which the dissociation of an ion is promoted by a supply of electrons; and an infrared multi-photon dissociation (IRMPD), in which the dissociation of an ion is promoted by irradiation with infrared laser light (see Non-Patent Literature 3, Patent Literature 1, or other documents).

It has been commonly known that dissociating the same precursor ion by a different dissociation technique produces different kinds of product ions and consequently yields a different kind of structural information on the ion. For example, according to Non-Patent Literature 4, using the CID for a glycopeptide in which a sugar chain is bound to a peptide yields information on the structure of the sugar chain, whereas using the ETD yields information on the peptide structure and information on the binding site of the sugar chain. Accordingly, it is possible to collectively obtain information on the sugar-chain structure, peptide structure and sugar-chain binding site by combining the result of an MS$^n$ analysis using the CID and that of an MS$^n$ analysis using the ETD, which allows for a detailed structural analysis of the glycopeptide. This holds true for not only the combination of CID and ETD but also for other combinations, such as the CID and ECD, or CID and HAD.

The previously described MS$^n$ analysis has the following problem:

Although any of the previously described techniques can induce dissociation of an ion, those techniques are significantly different in dissociation efficiency. For example, the target precursor ion can be almost entirely dissociated by changing the voltage or reaction time in the ion-exciting operation in the case of the CID, or by changing the laser power or period of irradiation with the laser light in the case of the IRMPD. In other words, the precursor-ion dissociation efficiency is almost 100%. By comparison, the precursor-ion dissociation efficiency in HAD, ECD and ETD is lower than in CID or other techniques. For example, Non-Patent Literature 5 reports that the precursor-ion dissociation efficiency in ECD is approximately 15% for peptides and approximately 30% for proteins.

Using such a dissociation technique whose precursor-ion dissociation efficiency is low means a corresponding decrease in the amount of product ions to be generated, which leads to a decrease in the detection sensitivity and in the signal-to-noise (SN) ratio of the signals, if obtained, originating from the product ions. Therefore, for example, it is possible that a peak corresponding to a product ion whose amount of generation is originally small becomes unobservable on the MS/MS spectrum.

FIGS. 7A and 7B show a comparison between an MS/MS spectrum obtained when CID was used as the ion dissociation technique, and one obtained when HAD was used. As shown in FIG. 7A, when CID is used, the signal intensity of the precursor ion becomes significantly low, while those of the product ions generally become high. On the other hand, as shown in FIG. 7B, when HAD is used, a considerable amount of precursor ion remains undissociated, so that the signal intensity of the precursor ion becomes high, while those of the product ions generally become low.

In order to improve the detection sensitivity and SN ratio of the signal, it is necessary to repeat the MS$^n$ analysis on the same sample multiple times and accumulate signal intensities respectively obtained in the individual MS$^n$ analyses. However, such an analysis consumes a considerable amount of sample and may exhaust the sample. Furthermore, if a sufficient amount of sample is not available, it is impossible obtain an MS/MS spectrum with a high level of quality. This may cause problems in the structural analysis of the target component or other tasks.

CITATION LIST

Patent Literature

Patent Literature 1: WO 2015/133259 A
Patent Literature 2: JP 2012-49056 A

Non Patent Literature

Non-Patent Literature 1: Raymond E. M., "An Introduction to Quadrupole Ion Trap Mass Spectrometry", *Journal of Mass Spectrometry*, Vol. 32, 1997, pp. 351-369
Non-Patent Literature 2: Ding L. and four other authors, "A digital ion trap mass spectrometer coupled with atmospheric pressure ion sources", *Journal of Mass Spectrometry*, Vol. 39, 2004, pp. 471-484
Non-Patent Literature 3: Lekha S. and another author, "Ion activation methods for tandem mass spectrometry", *Journal of Mass Spectrometry*, Vol. 39, 2004, pp. 1091-1112
Non-Patent Literature 4: Reiko Kiyonami and eight other authors, "Increased Selectivity, Analytical Precision, and Throughput in Targeted Proteomics", *Molecular & cellular proteomics*, 10.2, 2011
Non-Patent Literature 5: McFarland M. A. and four other authors, "Evaluation and Optimization of Electron Capture Dissociation Efficiency in Fourier Transform Ion Cyclotron Resonance Mass Spectrometry", *Journal of the American Society for Mass Spectrometry*, Vol. 16, 2005, pp. 1060-1066

SUMMARY OF INVENTION

Technical Problem

The present invention has been developed to solve the previously described problem. Its objective is to provide an ion trap mass spectrometer which can increase the detection sensitivity and SN ratio and of the detection signal, while suppressing the amount of use of the sample, when a dissociation technique whose precursor-ion dissociation efficiency is low is used for dissociating an ion, as well as to provide a mass spectrometric method using such a mass spectrometer.

Solution to Problem

The mass spectrometric method according to the present invention developed for solving the previously described problem is a mass spectrometric method using an ion trap mass spectrometer in which an ion of sample origin is captured within an inner space of an ion trap formed by a plurality of electrodes, the ion is dissociated by a predetermined ion dissociation technique, and the thereby generated product ions are ejected from the ion trap and detected, the mass spectrometric method including:

a) an ion selection step in which ions other than a target ion having a specific mass-to-charge ratio are ejected from the ion trap, among ions captured within the ion trap;

b) an ion dissociation-ejection step in which an ion-dissociating operation and an ion-ejecting operation are repeatedly performed multiple times, where the ion-dissociating operation includes dissociating, by the predetermined dissociation technique, the target ion maintained within the ion trap by the ion selection step, and the ion-ejecting operation includes ejecting ions having smaller mass-to-charge ratios than the mass-to-charge ratio of the target ion among the ions captured within the ion trap after the ion-dissociating operation while performing a mass scan in the direction in which the mass-to-charge ratio increases from the low mass-to-charge-ratio side, or in the opposite direction; and c) a mass spectrum creation step in which a mass spectrum is created based on a result of detection of the ions ejected from the ion trap during the ion-ejecting operation performed multiple times in the ion dissociation-ejection step.

The ion trap mass spectrometer according to the present invention developed for solving the previously described problem is a device for carrying out the previously described mass spectrometric method according to the present invention, which is an ion trap mass spectrometer in which an ion of sample origin is captured within an inner space of an ion trap formed by a plurality of electrodes, the ion is dissociated by a predetermined ion dissociation technique, and the thereby generated product ions are ejected from the ion trap and detected, the ion trap mass spectrometer including:

a) an ion selection executor for applying a predetermined voltage to at least one of the electrodes forming the ion trap, so as to eject ions other than a target ion having a specific mass-to-charge ratio from the ion trap, among ions captured within the ion trap;

b) an ion dissociation-ejection executor for repeatedly performing an ion-dissociating operation and an ion-ejecting operation multiple times, where the ion-dissociating operation includes dissociating, by the predetermined dissociation technique, the target ion maintained within the ion trap by an ion-selecting operation by the ion selection executor, and the ion-ejecting operation includes applying a predetermined voltage to at least one of the electrodes forming the ion trap, so as to eject ions having smaller mass-to-charge ratios than the mass-to-charge ratio of the target ion among the ions captured within the ion trap after the ion-dissociating operation while performing a mass scan in the direction in which the mass-to-charge ratio increases from the low mass-to-charge-ratio side, or in the opposite direction; and c) a mass spectrum creator for creating a mass spectrum based on a result of detection of the ions ejected from the ion trap during the ion-ejecting operation performed multiple times by the ion dissociation-ejection executor.

For example, the ion trap may be a triple quadrupole ion trap, linear ion trap, or the like. The predetermined ion dissociation technique is not specifically limited. Typical examples include the HAD, ETD, ECD and other techniques whose precursor-ion dissociation efficiency is low. Combining different types of dissociation techniques is also possible.

In the mass spectrometric method according to the present invention, for example, various ions generated from a sample in an ion source are introduced into the ion trap and captured by the radio-frequency electric field created within the inner space of the ion trap. In the ion selection step, a voltage applied to at least one of the electrodes forming the ion trap is controlled so as to eject and remove ions other than the target ion having a specific mass-to-charge ratio from the ion trap, among the ions captured within the ion trap. Consequently, only the target ion is maintained within the inner space of the ion trap.

Subsequently, in the ion dissociation-ejection step, an ion-dissociating operation is initially carried out for dissociating, by a predetermined dissociation technique, the target ion captured within the inner space of the ion trap. Understandably, the specific content of this ion-dissociating operation changes depending on the dissociation technique. For example, in the case of the HAD, the target ion captured within the ion trap is irradiated with hydrogen radicals supplied at a predetermined flow rate. The target ion is thereby dissociated into various product ions, which are then captured within the inner space of the ion trap. If a dissociation technique having a low dissociation efficiency is used, such as the HAD or ETD, or if the CID or similar dissociation technique is used under inappropriate dissociating conditions, such as a short reaction time, the target ion, i.e. the precursor ion, will partially remain at the point of completion of the ion-dissociating operation.

After the completion of the ion-dissociating operation, a voltage applied to at least one of the electrodes forming the ion trap is controlled so as to carry out an ion-ejecting operation for ejecting ions while performing a mass scan in the direction in which the mass-to-charge ratio increases from the low mass-to-charge-ratio side to a point located immediately before the mass-to-charge ratio of the target ion, or in the opposite direction. The mass scan is only performed over a mass-to-charge-ratio range which is lower than that of the target ion. Therefore, only the product ions resulting from the dissociation of the target ion are ejected, leaving the target ion intact within the inner space of the ion trap. During the ion-ejecting operation, the ions are ejected from the ion trap in ascending or descending order of mass-to-charge ratio. By sequentially detecting those ejected ions with a detector, an ion detection signal corresponding to each mass-to-charge ratio can be obtained.

The ion-ejecting operation performed in the previously described manner does not eject the target ion which has not been dissociated by the preceding ion-dissociating operation; this ion remains within the inner space of the ion trap. Accordingly, in the ion dissociation-ejection step, the ion-dissociating operation is once more performed on this remaining target ion, followed by the ion-ejecting operation for ejecting product ions generated by the dissociation. During this ion-ejecting operation, the ion intensity signal corresponding to each mass-to-charge ratio can be similarly obtained by sequentially detecting the ejected ions with the detector. The amount of target ion maintained within the inner space of the ion trap gradually decreases with each repetition of the ion-dissociating operation. Accordingly, the ion-dissociating operation and the ion-ejecting operation are repeated, for example, a specified number of times, or until the obtained ion intensity signal becomes equal to lower than a predetermined threshold. In the mass spectrum creation step, the final mass spectrum is created by accumulating the results of the detection of the ions ejected from the ion trap during the ion-ejecting operation performed multiple times, i.e. by accumulating mass spectrum information which shows the relationship between the mass-to-charge ratio and ion intensity signal.

Using the same dissociation technique (e.g. HAD) in the ion-dissociating operation performed multiple times yields a mass spectrum on which a specific kind of structural information corresponding to that dissociation technique is observed with high sensitivity. Using two or more different dissociation techniques (e.g. the HAD and CID) in the ion-dissociating operation performed multiple times yields a mass spectrum on which various kinds of structural information that cannot be obtained by a single analyzing method are observed. In the case of using two or more different dissociation techniques while performing the ion-dissociating operation multiple times, it is possible to create an individual mass spectrum for each dissociation technique instead of accumulating all data obtained for those different dissociation techniques. By this method, a plurality of mass spectra each of which shows a different kind of structural information can be obtained for one sample.

Advantageous Effects of Invention

With the mass spectrometric method and ion trap mass spectrometer according to the present invention, the target ion captured within the ion trap will not be wasted; the ion is dissociated multiple times, and the product ions generated by each dissociating operation are subjected to a mass spectrometric analysis. Eventually, a mass spectrum reflecting the results of the analysis is obtained. Even in the case where HAD, ETD, ECD or other dissociation techniques whose ion dissociation efficiency is low is used, it is possible to acquire a mass spectrum which has a high level of detection sensitivity and SN ratio of the signal intensity of the product ions, while suppressing the amount of use of the sample.

DESCRIPTION OF EMBODIMENTS

One embodiment of the mass spectrometric method and ion trap mass spectrometer according to the present invention is hereinafter described with reference to the attached drawings.

Figure 1:
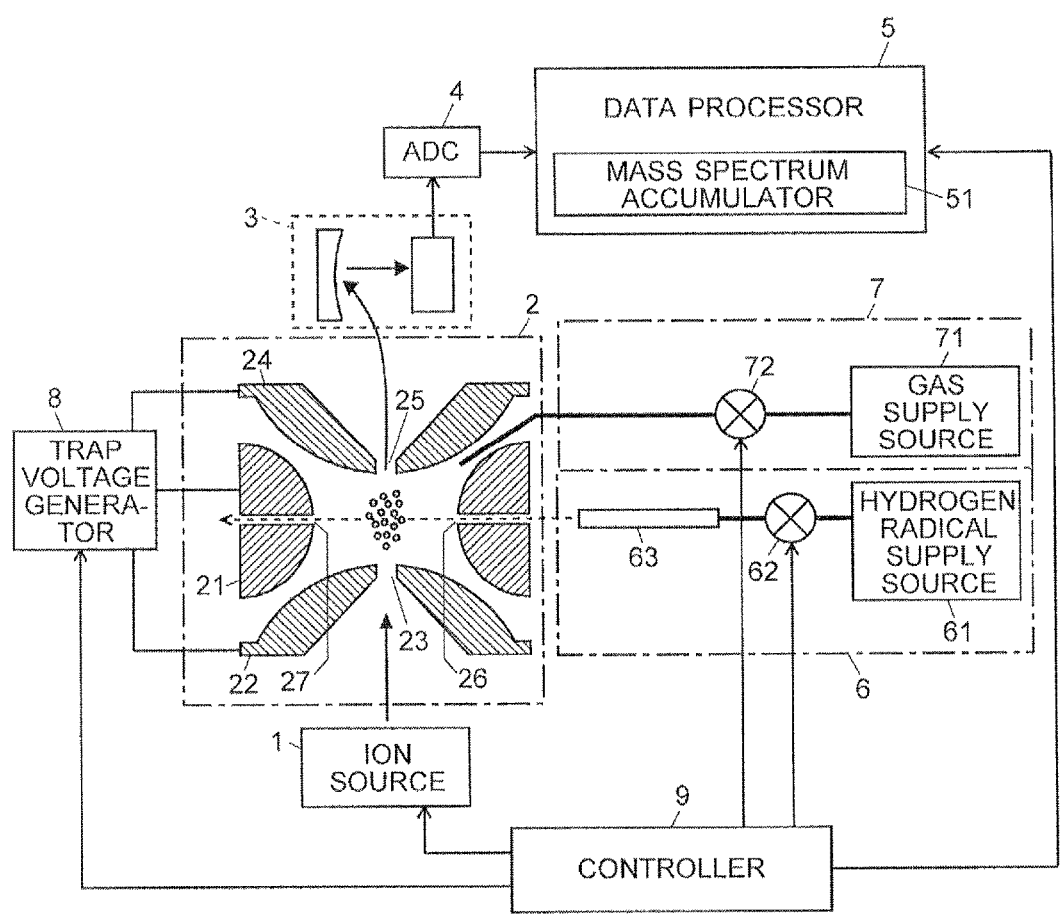
FIG. 1 is an overall configuration diagram of an ion trap mass spectrometer as one embodiment of the present invention.

FIG. 1 is an overall configuration diagram of the ion trap mass spectrometer according to the present embodiment.

The ion trap mass spectrometer according to the present embodiment has a vacuum chamber (not shown) in which vacuum atmosphere is maintained. The vacuum chamber contains: an ion source 1 for ionizing components in a target sample; an ion trap 2 for capturing ions generated by the ion source 1, by the effect of a radio-frequency electric field; a detector 3 for detecting ions ejected from the ion trap 2; an analogue-to-digital converter (ADC) 4 for digitizing detection signals produced by the detector 3; a data processor 5 for processing the obtained data; a hydrogen radical irradiator 6 for introducing hydrogen radicals into the ion trap 2 so as to dissociate ions within the ion trap 2 by hydrogen radical attachment dissociation (HAD); a gas introducer 7 for introducing a predetermined kind of gas, such as the cooling gas, into the ion trap 2; a trap voltage generator 8 for applying voltages to the electrodes forming the ion trap 2; and a controller 9 for controlling the operation of each component of the device.

The ion source 1 is an ion source which employs an appropriate ionization method, such as the matrix-assisted laser desorption/ionization (MALDI). The ion trap 2 is a three-dimensional quadrupole ion trap including a doughnut-shaped ring electrode 21 and a pair of endcap electrodes 22 and 24 facing each other across the ring electrode 21. According to a command from the controller 9, the trap voltage generator 8 applies voltages to the electrodes 21, 22 and 24, respectively, at a predetermined timing, the voltage being either a radio-frequency voltage or a direct-current voltage, or a voltage consisting of the combination of the two previously mentioned voltages. The hydrogen radical irradiator 6 includes: a hydrogen radical supply source 61 which holds or generates hydrogen radicals; a valve 62 with a controllable flow rate; and a nozzle 63 which is a heated tungsten capillary for ejecting hydrogen radicals in the form of a thin stream. The gas introducer 7 includes a gas supply source 71 and a valve 72 with a controllable flow rate. The data processor 5 includes a mass spectrum accumulator 51 as its functional block. A portion of the functions of the data processor 5 and controller 9 may be realized by executing, on a general-purpose personal computer, a dedicated processing-and-controlling software program previously installed on the same computer.

A normal MS/MS analysis operation in the ion trap mass spectrometer according to the present embodiment is hereinafter schematically described. Various ions generated from a target sample in the ion source 1 are ejected from the ion source 1 in a packet-like form and introduced into the ion trap 2 through an ion introduction hole 23 formed in the entrance endcap electrode 22. The sample-derived ions introduced into the ion trap 2 are captured by the radio-frequency electric field formed within the ion trap 2 by the radio-frequency voltage applied from the trap voltage generator 8 to the ring electrode 21. Subsequently, predetermined voltages are applied from the trap voltage generator 8 to the ring electrode 21 and other elements. This induces an excitation of ions which fall within specific ranges of mass-to-charge ratios that do not include the target ion having a specific mass-to-charge ratio. The excited ions are eventually removed from the ion trap 2. Thus, the target ion having a specific mass-to-charge ratio, i.e. the precursor ion, is selectively captured within the ion trap 2.

Subsequently, the valve 72 in the gas introducer 7 is opened to introduce inert gas, such as helium, as the cooling gas into the ion trap 2, whereby the precursor ion is cooled. Consequently, the precursor ion is focused into a smaller region around the center of the ion trap 2. In this state, the valve 62 in the hydrogen radical irradiator 6 is opened. A thin beam of hydrogen radicals (hydrogen atoms) is ejected from the nozzle 63. This beam passes through a radical particle introduction port 26 bored through the ring electrode 21. Thus, the hydrogen radicals are introduced into the ion trap 2, and the precursor ion captured within the ion trap 2 is irradiated with those hydrogen radicals. The opening of the valve 62 is previously adjusted so that the hydrogen radicals for irradiating the ion will be supplied at a flow rate equal to or higher than a predetermined value. The period of time of the irradiation with the hydrogen radicals is also appropriately set beforehand. Thus, the precursor ion undergoes radical-induced dissociation. As described in Patent Literature 1, when the sample is a peptide, c/z-type of product ions originating from the peptide are mainly generated.

The various product ions which have been generated are captured within the ion trap 2. Subsequently, under the control of the controller 9, the trap voltage generator 8 applies a predetermined radio-frequency voltage to the endcap electrodes 22 and 24 as well as other elements. The ions captured within the ion trap 2 are thereby excited in ascending or descending order of mass-to-charge ratio, to be eventually ejected through an ion ejection hole 25. The ions ejected from the ion trap 2 are detected by the detector 3. The detection signal is digitized by the ADC 4 and fed to the data processor 5. The data processor 5 creates an MS/MS spectrum based on the fed data, with the horizontal axis indicating the mass-to-charge ratio and the vertical axis indicating the ion intensity.

Although an MS/MS spectrum (product ion spectrum) for the target ion can be created by the previously described procedure, it is not always possible to obtain a mass spectrum having a high level of detection sensitivity and SN ratio of the signal, since the ion dissociation efficiency of the HAD is comparatively low, as noted earlier. Therefore, in the ion trap mass spectrometer according to the present embodiment, a characteristic MS/MS analysis is performed, as will be hereinafter described, so that a mass spectrum having a high level of detection sensitivity and SN ratio of the signal can be obtained.

Figure 2:
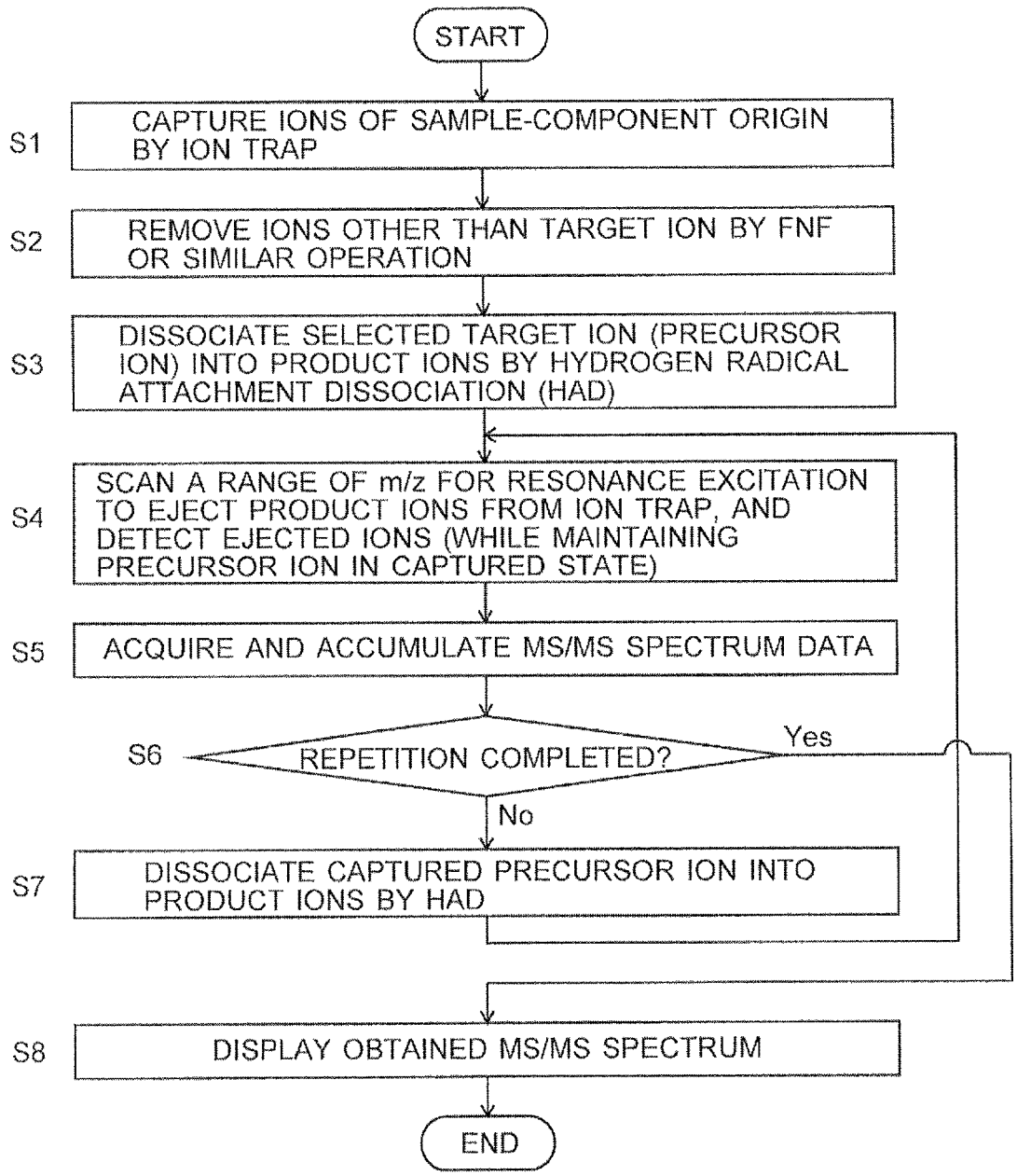
FIG. 2 is a flowchart of a characteristic MS/MS analysis operation in the ion trap mass spectrometer according to the present embodiment.

FIG. 2 is a flowchart of this MS/MS analysis operation. FIGS. 3A-3E are mass spectra (accumulated spectra) for explaining the present MS/MS analysis operation. It should be noted that FIGS. 3A-3E do not show measured results; they are conceptual diagrams showing accumulated spectra which are expected to be obtained if substance P is used as the sample.

Initially, various ions generated from the target sample in the ion source 1 are introduced into the inner space of the ion trap 2 and captured by the radio-frequency electric field (Step S1). Subsequently, a signal having a broad frequency spectrum with a notch at the oscillation frequency of the target ion (precursor ion) is applied to the endcap electrodes 22 and 24 to remove various unnecessary ions other than the target ion from the ion trap 2. A filtered noise field (FNF) signal is often used as such a broadband signal. Another commonly known example is the stored wave inverse Fourier transform (SWIFT) signal. The operation steps described thus far are the same as in the generally known MS/MS operation.

After the operation of selectively maintaining the target ion within the inner space of the ion trap 2 has been completed, the cooling of the target ion is performed, and hydrogen radicals are supplied from the hydrogen radical irradiator 6 into the ion trap 2 at a predetermined flow rate for a predetermined period of time, to irradiate the target ion with the hydrogen radicals and thereby promote its dissociation. The target ion is thereby dissociated into various product ions. Those product ions are captured within the inner space of the ion trap 2 along with the target ion which remains undissociated (Step S3).

Subsequently, under the control of the controller 9, the trap voltage generator 8 changes the voltages applied to the endcap electrodes 22 and 24 over a predetermined scan range so that the ions captured within the ion trap 2 are ejected from the ion trap 2 by resonance excitation in ascending order of mass-to-charge ratio. Unlike the conventional method in which the applied voltages are controlled to scan a wide range of mass-to-charge ratios including the mass-to-charge ratio of the target ion, the mass scan for the ion ejection in the present embodiment is performed in such a manner that the scan of the mass range of the ions to be ejected is started from the lowest mass-to-charge ratio and completed at an end point located immediately before the mass-to-charge ratio of the target ion, or more specifically, at a mass-to-charge ratio which is lower than the mass-to-charge ratio M of the target ion by a predetermined mass-to-charge-ratio difference $\Delta M$, i.e. M$-\Delta M$ (Step S4). This mass-to-charge-ratio difference $\Delta M$ can be previously determined, for example, based on the range of mass-to-charge ratios of the ions which are actually ejected when predetermined voltages for ejecting an ion having a specific mass-to-charge ratio are applied to the endcap electrodes 22 and 24. As noted earlier, it is also possible to perform the mass scan for the ejection by resonance excitation in the direction in which the mass-to-charge ratio decreases from the mass-to-charge ratio M$-\Delta M$, instead of performing the mass scan for the ejection by resonance excitation in the direction in which the mass-to-charge ratio increases. The former operation corresponds to the "forward scan" described in Patent Literature 2 or other documents. The latter operation corresponds to the "reverse scan".

While the range of mass-to-charge ratios of the ions to be ejected by resonance excitation is scanned in the previously described manner, the detector 3 detects the ions ejected from the ion trap 2. The detection signals are converted into digital data, which are fed to the data processor 5 and temporarily stored in a built-in memory of the mass spectrum accumulator 51. Those data represent an MS/MS spectrum which shows the relationship between the mass-to-charge ratio and ion intensity of the product ions within a mass-to-charge-ratio range that is lower than the mass-to-charge ratio of the target ion (Step S5).

Figure 3:
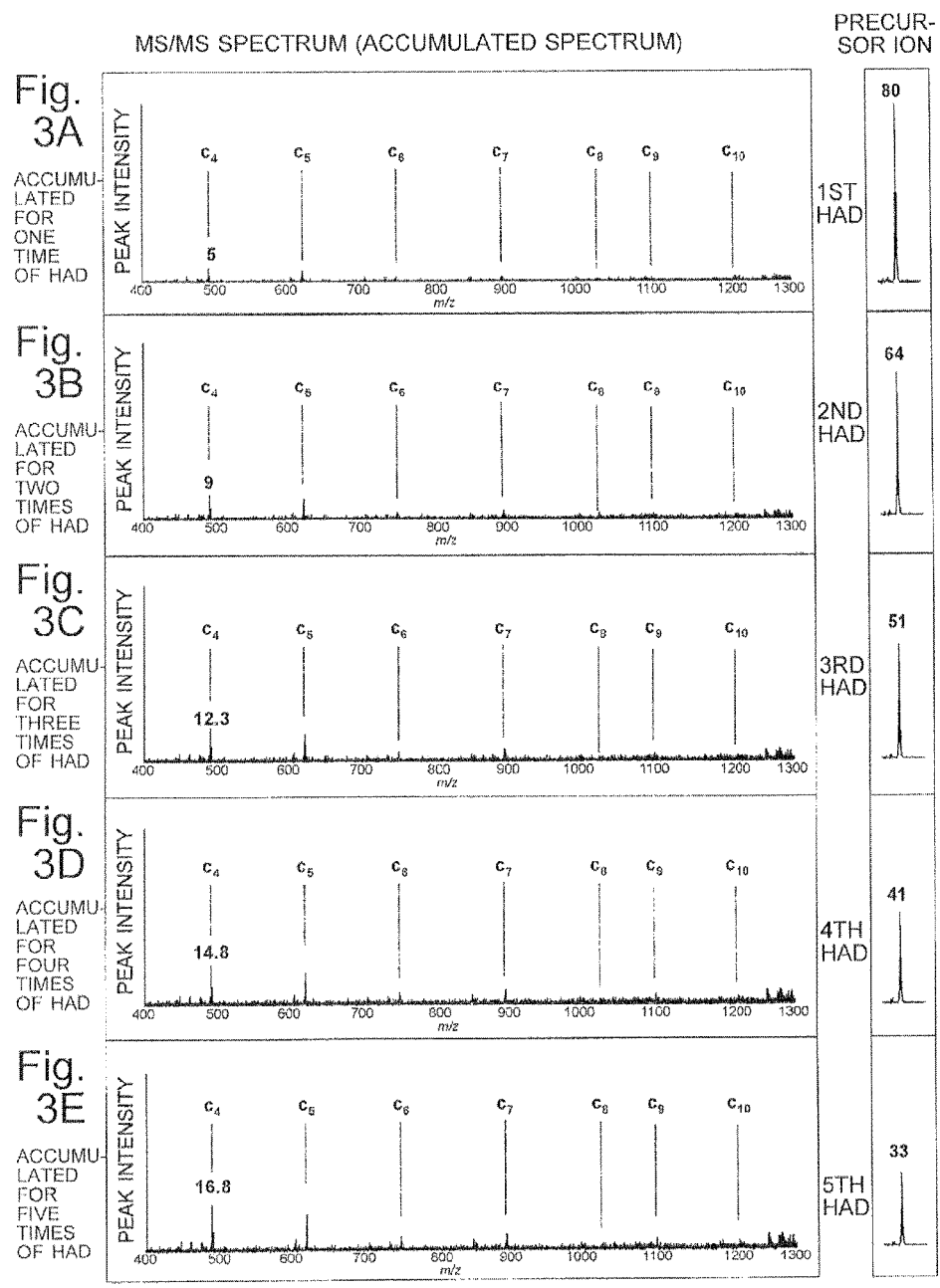
FIGS. 3A-3E are mass spectra (accumulated spectra) for explaining the MS/MS analysis operation in the ion trap mass spectrometer according to the present embodiment.

The example shown in FIGS. 3A-3E is a case in which the dissociation efficiency for the precursor ion by HAD was assumed to be 20%, and the ratio of the generated amount of C4-type ion to the amount of precursor ion was assumed to be 25%. The numerical values indicated on or above the peak of the precursor ion and the peak of product ion c4 indicate the amounts of those ions in arbitrary unit. As shown in FIG. 3A, after the completion of the first HAD, the peak intensities of the product ions on the spectrum are low, since only 20% of the captured target ion is dissociated into product ions.

By the previously described operation for the ejection by resonant excitation, the product ions within the mass-to-charge-ratio range lower than the mass-to-charge ratio of the target ion are removed from the ion trap 2, whereas the target ion which was not dissociated in the preceding HAD operation is not removed but remains almost intact within the ion trap 2. Accordingly, the controller 9 determines, for example, whether or not the operations in Steps S4 and S5 have been repeated a predetermined number of times (Step S6). If the predetermined number of times has not been reached yet, the operation proceeds to Step S7. In this step, similar to Step S3, hydrogen radicals are supplied from the hydrogen radical irradiator 6 into the ion trap 2 at a predetermined flow rate for a predetermined period of time to irradiate the target ion with the hydrogen radicals and thereby promote its dissociation. At least a portion of the remaining target ion is thereby dissociated into various product ions. Those product ions are captured within the inner space of the ion trap 2 along with the target ion which remains undissociated.

After the ion dissociation in Step S7 is completed, the operation returns to Step S4 to once more perform the ejection by resonance excitation and the detection of the ions ejected from the ion trap 2. Once again, a set of data is obtained which represents an MS/MS spectrum showing the relationship between the mass-to-charge ratio and ion intensity of the product ions within a mass-to-charge-ratio range that is lower than the mass-to-charge ratio of the target ion. The mass spectrum accumulator 51 adds the newly acquired spectrum data to the spectrum data already stored in the memory for each mass-to-charge ratio, and replaces the content of the memory with the data obtained by the addition (Step S5).

The operations and processing in Steps S4 through S7 are repeated until it is determined in Step S6 that the number of repetitions has reached the predetermined number. For example, if the predetermined number of repetitions is five, the ion-dissociating operation is performed five times, and the mass spectrum accumulator 51 acquires MS/MS spectrum data by totaling all ion intensities of the product ions generated in each ion-dissociating operation. That is to say, the peak intensity of the product ions on the MS/MS spectrum (accumulated spectrum) gradually increases with each execution of the HAD operation, as shown in FIGS. 3B-3E.

When it has been determined in Step S6 that the number of repetitions has reached the predetermined number, the operations on the ions are discontinued, and an MS/MS spectrum based on the accumulated MS/MS spectrum data which have been obtained in the mass spectrum accumulator 51 at that point in time is displayed, for example, on a display unit, which is not shown (Step S8). The displayed MS/MS spectrum reflects the product ions generated by the dissociation of a considerable portion or almost the entirety of the target ion derived from the sample. Therefore, an MS/MS spectrum having a high level of SN ratio of the signal as well as a high level of detection sensitivity can be obtained even in the case of using an ion dissociation technique whose ion dissociation efficiency is low, as with the HAD.

In the previous description, it is determined in Step S6 whether or not the operations of Steps S4 and S5 have been repeated the predetermined number of times. A different method may be used to determine whether or not the repetition should be discontinued. For example, the repetition may be discontinued when the sum of the signal intensities of all detected product ions has become equal to or less than a predetermined threshold. In any case, the repetition can be discontinued when the amount of target ion held within the ion trap 2 has decreased to such a low level that it is no longer possible to expect that a significant increase in signal intensity can be achieved by further repeating the ion-dissociating operation and the ion-ejecting operation. In the case where the measurement time is limited, the repetition may be discontinued when the measurement time has exceeded a predetermined time limit.

A measurement result obtained by the previously described characteristic MS/MS analysis is hereinafter described. Substance P (molecular weight: 1347.6) was used as the sample for the measurement, and $\alpha$-Cyano-4-hydroxycinnamic acid (CHCA) was used as the matrix for preparing the sample for MALDI. A digital ion trap mass spectrometer equipped with a mechanism for irradiating ions with hydrogen-radical particles similar to the system shown in FIG. 1 was used as the ion trap mass spectrometer for the measurement.

Figure 4:
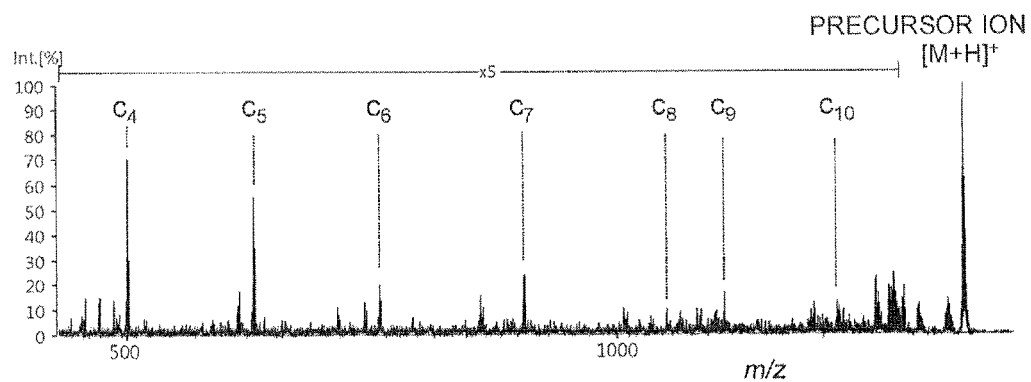
FIG. 4 is a measured example of the mass spectrum for substance P in the ion trap mass spectrometer according to the present embodiment.

FIG. 4 is a measured example of an MS/MS spectrum for substance P obtained by a normal MS/MS analysis by HAD (i.e. in which the HAD operation was performed only one time). In FIG. 4, in addition to a series of c-type product ions, the precursor ion is also observed with a high level of intensity. This means that only a portion of the precursor ion captured within the ion trap has been dissociated by HAD.

Figure 5:
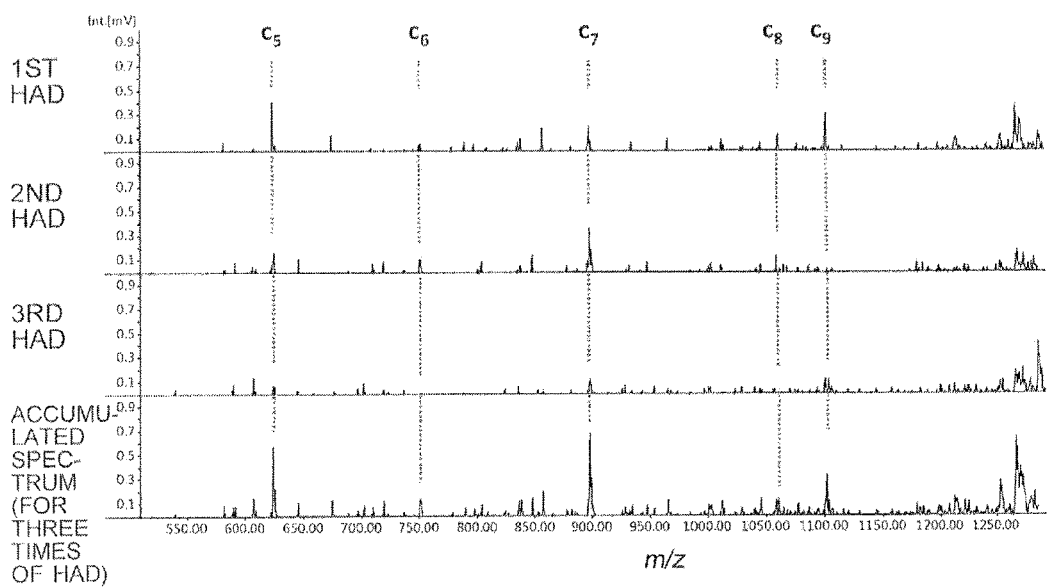
FIG. 5 is a measured example of the mass spectra for substance P obtained by repeating a HAD operation three times in the ion trap mass spectrometer according to the present embodiment.
Figure 6:
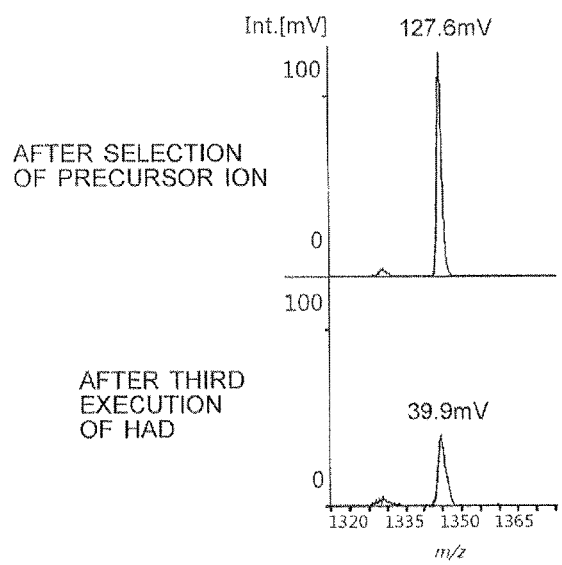
FIG. 6 shows a change in the amount of precursor ion observed when the data shown in FIG. 4 were acquired.
Figure 7A:
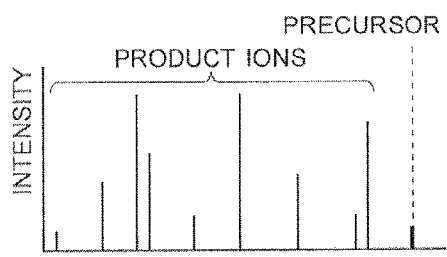
FIGS. 7A and 7B show a comparison between a mass spectrum obtained by when CID was used as the ion dissociation technique and one obtained when HAD was used.
Figure 7B:
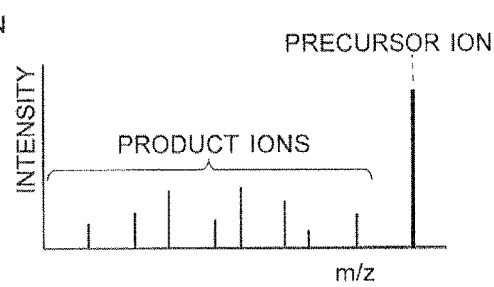

FIG. 5 is a measured example of MS/MS spectra obtained by the previously described procedure of the characteristic MS/MS analysis, in which the HAD operation was repeated three times, with one MS/MS spectrum for substance P obtained each time and an MS/MS spectrum obtained by accumulating those MS/MS spectra. FIG. 6 shows an actually measured mass spectrum for the precursor ion after the selection of the precursor ion and one for the precursor ion which was remaining after the third execution of the HAD operation. It should be noted that the peak of the precursor ion as shown in FIG. 6 cannot be observed in the first and second executions of the HAD operation, since only the product ions are thereby ejected from the ion trap for detection.

The measured result shown in FIG. 5 demonstrates that, although the dissociation efficiency for the precursor ion and the amount of the detected product ions varied with each execution of the HAD operation, a mass spectrum with a high level of SN ratio was obtained by accumulating the mass spectra individually obtained by repeating the HAD operation three times for the precursor ion obtained by a single ionizing operation. If a conventional method for MS/MS analysis were used, it would be necessary to repeat the ionizing operation in the ion source three times to obtain an accumulated mass spectrum which is similar to the present example. With the characteristic method for MS/MS analysis according to the present embodiment, only a single execution of the ionizing operation is needed to obtain a comparable mass spectrum. This means that the amount of sample required for obtaining a mass spectrum with a comparable level of SN ratio will be decreased to one third. Accordingly, the method according to the present embodiment can be considered to be particularly useful when only a small amount of sample is available, or when the sample is expensive (or rare).

The previously described embodiment has been concerned with the case of using HAD to dissociate a target ion captured within the ion trap 2. It is evident that the same technique as described in the previous embodiment can also be employed to improve the quality of the MS/MS spectrum in the case of using ETD or ECD for dissociation, both of which have a low level of precursor-ion dissociation efficiency as with the HAD. In addition, in the case of using CID or IRMPD, both of which have a high level of precursor-ion dissociation efficiency, it may be impossible to sufficiently improve the dissociation efficiency, depending on the dissociating conditions. For example, in the case of the IRMPD, it may be impossible to sufficiently increase the laser power due to a restriction on the device. It is evident that the previously described technique can be employed in such a case to improve the quality of the MS/MS spectrum.

It is also possible to sequentially perform a plurality of different types of dissociating operations for a precursor ion generated by a single ionizing operation, instead of repeating a single type of dissociating operation, such as the HAD.

As noted earlier, using a different dissociating technique for the same precursor ion may cause the precursor ion to be dissociated at different bonds and produce different kinds of product ions. Therefore, an appropriate combination of ion dissociation techniques which yield different combinations of product ions can provide a wider variety of structural information on the ion and consequently improve the accuracy of the structural analysis of the ion.

For example, in the case of the structural analysis of a glycopeptide, an MS/MS analysis employing the CID or IRMPD primarily yields information on the peptide sequence and the sugar-chain structure. On the other hand, an MS/MS analysis employing the HAD, ECD or ETD yields information on the peptide sequence and the binding site of the sugar chain. Accordingly, for a glycopeptide ion, the HAD may be used during one or more executions of the ion-dissociating operation from the beginning, while the CID is used in the subsequent executions for the precursor ion remaining in the ion trap. Two sets of product ions corresponding to the HAD and CID are thereby obtained for the precursor ion generated by a single ionization of the sample. This improves the accuracy of the structural analysis of the glycopeptide. The accumulated spectrum may be constructed by accumulating both the MS/MS spectra obtained by the HAD and those obtained by the CID. It is also possible to separately acquire one MS/MS spectrum by the HAD and one MS/MS spectrum by the CID to decrease the complexity of the data analysis.

The previous embodiment and other variations are mere examples of the present invention. Any change, addition or modification appropriately made within the spirit of the present invention in any aspects other than those already described will naturally fall within the scope of claims of the present application.

REFERENCE SIGNS LIST

1 . . . Ion Source
2 . . . Ion Trap
21 . . . Ring Electrode
22, 24 . . . Endcap Electrode
23 . . . Ion Introduction Hole
25 . . . Ion Ejection Hole
26 . . . Radical Particle Introduction Port
3 . . . Detector
4 . . . Analogue-to-Digital Converter
5 . . . Data Processor
51 . . . Mass Spectrum Accumulator
6 . . . Hydrogen Radical Irradiator
61 . . . Hydrogen Radical Supply Source
62 . . . Valve
63 . . . Nozzle
7 . . . Gas Introducer
71 . . . Gas Supply Source
72 . . . Valve
8 . . . Trap Voltage Generator
9 . . . Controller

The invention claimed is:

1. A mass spectrometric method using an ion trap mass spectrometer in which an ion of sample origin is captured within an inner space of an ion trap formed by a plurality of electrodes, the ion is dissociated by a predetermined ion dissociation technique, and thereby generated product ions are ejected from the ion trap and detected, the mass spectrometric method comprising:

a) an ion selection step in which ions other than a target ion having a specific mass-to-charge ratio are ejected from the ion trap, among ions captured within the ion trap;

b) an ion dissociation-ejection step in which an ion-dissociating operation and an ion-ejecting operation are repeatedly performed multiple times, where the ion-dissociating operation includes dissociating, by the predetermined dissociation technique, the target ion maintained within the ion trap by the ion selection step, and the ion-ejecting operation includes ejecting ions having smaller mass-to-charge ratios than the mass-to-charge ratio of the target ion among the ions captured within the ion trap after the ion-dissociating operation while performing a mass scan in a direction in which the mass-to-charge ratio increases from a low mass-to-charge-ratio side, or in an opposite direction; and c) a mass spectrum creation step in which a mass spectrum is created based on a result of detection of the ions ejected from the ion trap during the ion-ejecting operation performed multiple times in the ion dissociation-ejection step.

2. The mass spectrometric method according to claim 1, wherein:

the ion-ejecting operation in the ion dissociation-ejection step is performed in such a manner as to sequentially eject the ions captured within the ion trap while performing the mass scan in the direction in which the mass-to-charge ratio increases from the low mass-to-charge-ratio side to a point located immediately before the mass-to-charge ratio of the target ion.

3. The mass spectrometric method according to claim 2, wherein:

the ion dissociation technique includes one technique selected from hydrogen radical attachment dissociation, electron transfer dissociation, and electron capture dissociation.

4. The mass spectrometric method according to claim 1, wherein:

the ion dissociation technique includes one technique selected from hydrogen radical attachment dissociation, electron transfer dissociation, and electron capture dissociation.

5. The mass spectrometric method according to claim 4, wherein:

a same ion dissociation technique is used in the ion-dissociating operation repeatedly performed multiple times in the ion dissociation-ejection step.

6. The mass spectrometric method according to claim 4, wherein:

two or more different ion-dissociating techniques are used in the ion-dissociating operation repeatedly performed multiple times in the ion dissociation-ejection step.

7. An ion trap mass spectrometer in which an ion of sample origin is captured within an inner space of an ion trap formed by a plurality of electrodes, the ion is dissociated by a predetermined ion dissociation technique, and thereby generated product ions are ejected from the ion trap and detected, the ion trap mass spectrometer comprising:

a) an ion selection executor for applying a predetermined voltage to at least one of the electrodes forming the ion trap, so as to eject ions other than a target ion having a specific mass-to-charge ratio from the ion trap, among ions captured within the ion trap;

b) an ion dissociation-ejection executor for repeatedly performing an ion-dissociating operation and an ion-ejecting operation multiple times, where the ion-dissociating operation includes dissociating, by the predetermined dissociation technique, the target ion maintained within the ion trap by an ion-selecting operation by the ion selection executor, and the ion-ejecting operation includes applying a predetermined voltage to at least one of the electrodes forming the ion trap, so as to eject ions having smaller mass-to-charge ratios than the mass-to-charge ratio of the target ion among the ions captured within the ion trap after the ion-dissociating operation while performing a mass scan in a direction in which the mass-to-charge ratio increases from a low mass-to-charge-ratio side, or in an opposite direction; and c) a mass spectrum creator for creating a mass spectrum based on a result of detection of the ions ejected from the ion trap during the ion-ejecting operation performed multiple times by the ion dissociation-ejection executor.

* * * * *